United States Patent [19]

Foley

[11] 4,422,977

[45] Dec. 27, 1983

[54] HYDROESTERIFICATION OF 1-ALKENE

[75] Inventor: Paul Foley, Summit, N.J.

[73] Assignee: Celanese Corporation, New York, N.Y.

[21] Appl. No.: 342,636

[22] Filed: Jan. 26, 1982

[51] Int. Cl.³ .................................. C07C 153/017
[52] U.S. Cl. ....................................... 260/455 R
[58] Field of Search ............................... 260/455 R

[56] References Cited

U.S. PATENT DOCUMENTS 2,863,911  12/1958  Büchner et al. ............. 260/455 R Primary Examiner—John M. Ford
Assistant Examiner—Robert C. Whittenbaugh
Attorney, Agent, or Firm—Depaoli & O'Brien

[57] ABSTRACT

This invention provides a process for hydroesterification of an alpha-olefin with carbon monoxide and hindered thiol compound, in the presence of a catalyst which is a stabilized complex of palladium and tertiary phosphine ligand.

29 Claims, 1 Drawing Figure

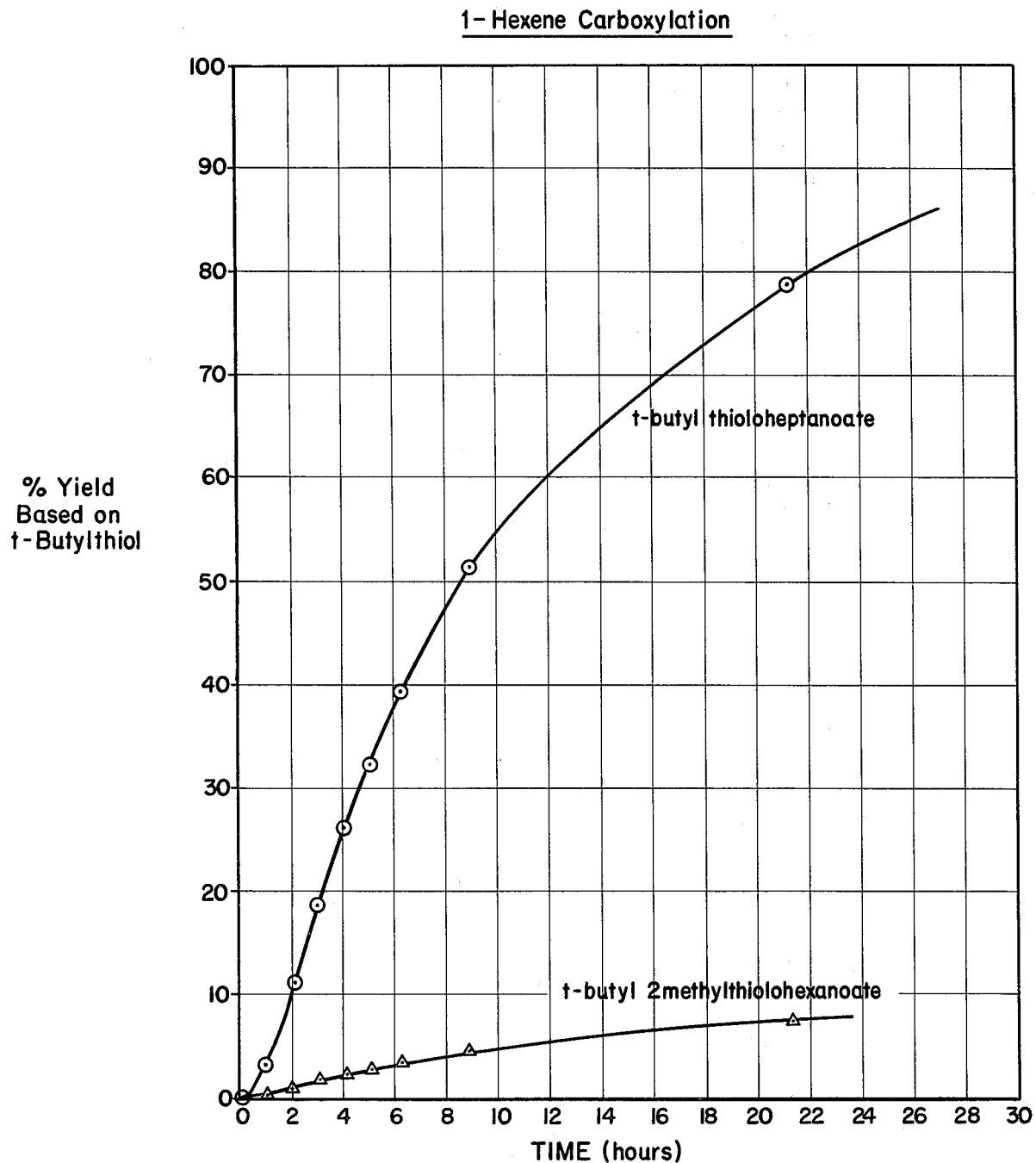

HYDROESTERIFICATION OF 1-ALKENE

BACKGROUND OF THE INVENTION

Catalytic carbonylation of olefinic and acetylenic compounds to form oxygenated derivatives with an increased content of carbon atoms is a well-established technology. Various developments and improvements are described in U.S. patents such as U.S. Pat. Nos. 2,768,968; 2,863,911; 2,876,254; 3,040,090; 3,455,989; 3,501,518; 3,507,891; 3,652,655; 3,660,439; 3,700,706; 3,723,486; 3,746,747; 3,755,419; 3,755,421; 3,793,369; 3,856,832; 3,859,319; 3,887,595; 3,906,015; 3,917,677; 3,952,034; 3,992,423; 4,102,920; 4,245,115; 4,246,183; and references cited therein.

Of particular interest with respect to the present invention is the chemical literature relating to hydroesterification of alpha-olefins to yield alkanoate esters.

In J. Org. Chem., 41, 793(1976) and J. Org., Chem., 41, 2885(1976) there is reported the synthesis of linear carboxylate esters from alpha-olefins in the presence of a homogeneous platinum complex catalyst:

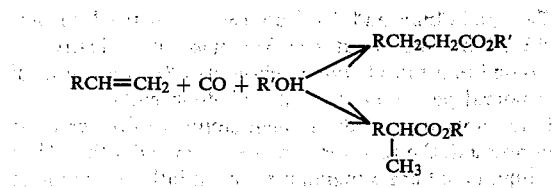

U.S. Pat. No. 3,933,884 describes a process for preparing thioloesters by the interaction of an alpha-olefin with carbon monoxide and a thiol compound in the presence of a catalyst composed of a noble metal halide and a Group IVB metal halide and a Group VB donor ligand.

There is continuing development effort directed to improvement of processes and catalysts for carbonylation and hydroesterification of olefinic substrates to yield oxygenated or sulfurated derivatives of increased carbon content via monomeric and dimeric reaction mechanisms.

Accordingly, it is a main object of this invention to provide an improved process for conversion of aliphatic alpha-olefins into fatty acid derivatives.

It is another object of this invention to provide a process for producing alkyl thioloalkanoate by hydroesterification of 1-alkene with improved conversion and selectivity.

It is a further object of this invention to provide a stabilized palladium catalyst solution adapted for hydroesterification of olefinic hydrocarbons.

Other objects and advantages of the present invention shall become apparent from the accompanying description and illustrative processing data.

DESCRIPTION OF THE INVENTION

One or more objects of the present invention are accomplished by the provision of a process for hydroesterification of 1-alkene which comprises (1) reacting 1-alkene with carbon monoxide and hindered thiol compound in a liquid medium containing a halide-free catalyst complex of palladium and tertiary phosphine ligand; and (2) recovering alkyl thioloalkanoate product.

The term "1-alkene" is meant to include aliphatic alpha-olefins which contain between about 2-12 carbon atoms, and which can contain heteroatoms such as oxygen, sulfur, nitrogen and halogen which do not interfere with the invention process hydroesterification reaction. Illustrative of suitable alpha-olefins are propene, 1-butene; 1-pentene; 1-hexene; 1,4-hexadiene; 6-chloro-1-hexene; 6-methyl-1-heptene; vinylcyclohexane; 1-dodecene; and the like. Normal 1-alkene compounds are preferred because they can be converted to straight chain fatty acid derivatives which are adapted for application as synthetic lubricants.

The present invention process is highly selective in reactivity, and is restricted to the hydroesterification of alpha-olefins. For example, 1-hexene reacts efficiently under the processing conditions, while 2-hexene is inert under the same conditions.

An important aspect of the present invention is the use of a hindered thiol compound in the hydroesterification reaction. The term "hindered thiol" is meant to include secondary and tertiary thiol compounds which are reactive with 1-alkene compounds under the hydroesterification conditions. Thiol compounds which are not "hindered" have little or no reactivity with 1-alkene compounds for purposes of hydroesterification. Thus, tertiary-butylthiol reacts smoothly with 1-hexene under the processing conditions, while 1-butanethiol is essentially unreactive under the same conditions.

Illustrative of suitable hindered thiol compounds are secondary and tertiary thiols containing between about 3-30 carbon atoms and 1-2 thiolo groups, such as 2-propanethiol; 2-butanethiol; 1,1-dimethylethanethiol; 2,4-pentanedithiol; 2-decanethiol; 3-tridecanethiol; 2-eicosanethiol; cyclohexanethiol; 1,1,1-triphenylmethanethiol; and the like.

The thiol and 1-alkene and carbon monoxide coreactants can be employed in essentially any proportions as dictated by practical considerations of economy and convenience. The presence of the three coreactants per se in a reactor system satisfies the stoichiometry of the process, notwithstanding that any one coreactant may be present in molar excess relative to the other coreactants.

It is preferred that the carbon monoxide is introduced into the process reaction system up to a partial pressure of between about 300 and 2000 psi of carbon monoxide. The carbon monoxide environment in the process system can contain one or more inert gases such as nitrogen, helium, argon, and the like. For optimal results it is essential that the process is conducted in a deoxygenated environment, so as not to affect adversely the 1-alkene conversion rate and the selective yield of alkyl thioloalkanoate product.

The liquid medium in the first step of the process can include a solvent diluent, in addition to the other liquid constituents in the hydroesterification reaction system. Suitable solvents include propane, butane, pentane, cyclopentane, hexane, cyclohexane, heptane, octane, tetradecane, petroleum refinery light hydrocarbon mixtures, benzene, chlorobenzene, nitrobenzene, toluene, xylene, mesitylene, tetrahydrofuran, dimethylformamide, methyl ethyl ketone, the thioester product, and the like.

A further aspect of the present invention is the provision of a stabilized catalyst which is highly selective for hydroesterification of alpha-olefin compounds. Thus, in another embodiment the present invention provides a catalyst composition consisting of a solvent solution of solute components comprising a halide-free complex of palladium salt and tertiary phosphine ligand which is in contact with a stabilizing quantity of thiol compound.

The "solvent" in the said stabilized catalyst composition can comprise an inert solvent diluent of the type previously described, and/or 1-alkene and/or tertiary phosphine, and the like. The said catalyst composition can be preformed prior to introduction into a hydroesterification zone, or it can be formed in situ by the separate introduction of the palladium salt, tertiary phosphine ligand and thiol components into the carbonylation reaction zone.

The palladium component of the catalyst composition preferably is introduced in the form of a palladium-containing compound such as palladium acetate, palladium propionate, palladium acetylacetonate, bis-(1,5-diphenyl-3-pentadienone) palladium(o), palladium nitrate, palladium sulfate, and the like. The palladium can be in either a plus two or zero valent state.

It is highly preferred that the catalyst composition is halide-free, e.g., any halide-containing salt such as palladium(II) chloride is excluded. An important advantage of a "halide-free" catalyst complex is the prevention of a highly corrosive reaction environment.

With reference to the tertiary phosphine ligand, the term "phosphine" is meant to include corresponding phosphite derivatives. Illustrative of suitable tertiary phosphine ligands are triisopropylphosphine, tri-n-butylphosphine, triisobutylphosphine, tri-n-octylphosphine, tricyclohexylphosphine, triphenylphosphine, tritolylphosphine, tribenzylphosphine, and the corresponding phosphite compounds. The substituents in the tertiary phosphine ligands can be the same or different, and mixtures of tertiary phosphine ligands can be employed. Illustrative of a ligand mixture is one containing about 70–99 mole percent trialkylphosphine (e.g., triisopropylphosphine) and about 1–30 mole percent triarylphosphine (e.g., triphenylphosphine). A preferred class of tertiary phosphine ligands are trialkylphosphines in which each alkyl group contains between 2 and about 8 carbon atoms.

It appears that a specific type of palladium/tertiary phosphine complex catalyst exhibits a superior combination of properties with respect to hydroesterification of 1-alkene in comparison with a complex of palladium and some other tertiary phosphine ligand, i.e., the preferred catalyst contains a trialkylphosphine ligand which has a ΔHNP basicity between about 70–350 and a steric parameter $\theta$ between about 136°–190°. Illustrative of this category of trialkylphosphines are triisopropylphosphine, tri-secondary-butylphosphine and triisobutylphosphine.

For example, palladium/triisopropylphosphine complex provides a better balance of conversion and selectivity as a catalyst in the present invention process than does any of palladium/tri-n-propylphosphine complex, palladium/tri-n-butylphosphine complex, palladium/diethylphenylphosphine complex, palladium/tricyclohexylphosphine complex, or palladium/triphenylphosphine complex, respectively.

By the term "ΔHNP" is meant the difference in the half neutralization potential between the liquid under consideration and N,N'-diphenylquanidine as determined in accordance with the procedure described in Analytical Chemistry, 32, 985–987 (1960). The ΔHNP of 24 tertiary phosphines are listed in U.S. Pat. No. 3,527,809.

By the term "steric parameter $\theta$" is meant the apex angle of a cylindrical cone, centered 2.28 Å from the center of the phosphorus atom, which touches the Van der Waals radii of the outermost atoms of the hydrocarbyl substituents [C. A. Tolman, J. Amer. Chem. Soc., 92, 2953 (1970); Ibid, 92, 2956 (1970); and Ibid, 96, 53 (1974)].

It appears that the superior catalytic properties of a palladium/triisopropylphosphine type of catalyst complex are attributable to the specifically inherent basicity and steric structure of triisopropylphosphine as a complexing ligand. It is believed that the physicochemical properties of triisopropylphosphine favor the formation of a highly active form of complexed palladium catalyst for the purposes of hydroesterification of 1-alkene compounds.

The catalyst complex of palladium salt/tertiary phosphine is provided in the hydroesterification reaction medium in at least a catalytic quantity, and the mole ratio of 1-alkene to catalyst complex preferably is at least 1:1 or higher.

The palladium and tertiary phosphine ligand in the hydroesterification zone liquid reaction medium typically are provided in a ratio between about 1–20 moles of tertiary phosphine ligand per gram atom of palladium metal.

The palladium and thiol compound in the hydroesterification zone liquid reaction medium typically are provided in a ratio between about 1–100 moles of thiol compound per gram atom of palladium metal.

It has been observed that the reactivity of the catalyst complex and the reaction rate are enhanced if the pH of the liquid medium is maintained in a mildly acidic range during the hydroesterification reaction, e.g., a pH in the range between about 1–6. In addition, the hydroesterification proceeds in a more predictable and reproducible manner when the pH of the reaction medium is in the acidic range. It is believed that the acidic pH promotes the presence of a favorable catalyst species.

A convenient means of establishing a desirable acidic pH range is by the inclusion of a soluble organic acid in the liquid medium, e.g., acetic acid, p-toluenesulfonic acid, or the like. It appears that optimal reactivity of the catalyst complex is favored by controlling the acidic pH with an acidic compound which is characterized by a poor ligating anion, e.g., a carboxylate anion.

It is highly preferred that the stabilized catalyst complex in the reaction system is "halide-free". Among the disadvantages of a catalyst complex containing a halide component (e.g., in the form of palladium (II) chloride) is the consequential corrosion of metal surfaces in the reactor system containing the catalyst halide component.

It is also preferred to conduct the hydroesterification step of the invention process in the presence of a polymerization inhibitor, e.g., hydroquinone. If an inhibitor is not included in the reaction system then there is an increased incremental loss of 1-alkene to polymeric byproducts. When a polymerization inhibitor is employed, the yield of byproducts can be limited to less than about 10 percent.

The temperature for the first step hydroesterification reaction can vary in the range between about 50° C. and 180° C., and preferably is in the range between about 80° C. and 130° C.

The pressure in the first step reaction zone can vary in the range between about 300 and 3000 psi, and preferably is in the range between about 500 and 1500 psi. As previously indicated, it is advantageous to provide a carbon monoxide partial pressure in the range between about 300 and 2000 psi in the first step reaction zone.

In a typical batch type process, the reaction time for the hydroesterification step will average in the range between about 0.5 and 50 hours, as determined by temperature and pressure parameters and the reactivity of the palladium-phosphine complex catalyst.

After the completion of the first step hydroesterification reaction, the liquid product mixture is cooled to room temperature or lower. Any high molecular weight polyene byproducts in the reaction product mixture tend to precipitate out during the cooling stage. As necessary, the reaction product mixture can be filtered to remove polymeric precipitate.

The product mixture is then fractionated by a conventional method such as distillation to recover the alkyl thioloalkanoate product. It is highly advantageous to leave some alkyl thioloalkanoate as a residual solvent medium for the catalyst complex which is in solution. The said solvent solution of catalyst can be recycled to the carbonylation step of the process.

In a batch type process, it is convenient and advantageous to perform several hydroesterification runs successively in the same reactor system, without recovery of alkyl thioloalkanoate product between the respective runs. The accumulated product is recovered after the completion of the last run.

In another embodiment, this invention contemplates a continuous process for producing and recovering alkyl thioloalkanoate. Illustrative of a specific application of the continuous process, a solution of palladium-phosphine complex and thiol is fed continuously to a first reaction zone of an elongated reactor system, simultaneously with the introduction of 1-alkene. In the first reaction zone, the feed materials are admixed efficiently with each other and with carbon monoxide which is present at a partial pressure of at least 300 psi (e.g., 400-700 psi). The admixture is passed into a second reaction zone of the reactor system, and the temperature and flow rates are controlled in the second reaction zone so that optimal proportions of 1-alkene and carbon monoxide are reacted.

A product stream is removed continuously from the end of the second reaction zone. The product stream is distilled to remove a portion of the alkyl thioloalkanoate product. The residual solution of product and catalyst is recycled to the first reaction zone of the hydroesterification system.

In a typical run, the 1-alkene conversion is 60–65 percent and the selectivity to alkyl thioloalkanoate is 80–85 percent.

At 100° C. and 750 psi carbon monoxide pressure, tertiary-butyl thioloheptanoate can be produced from 1-hexene and tertiary-butylthiol with a space-time yield of 13–31 grams per liter-hour, a Linear/Branched ratio of about 20/1, and about 5 percent 1-hexene isomerization to internal hexenes.

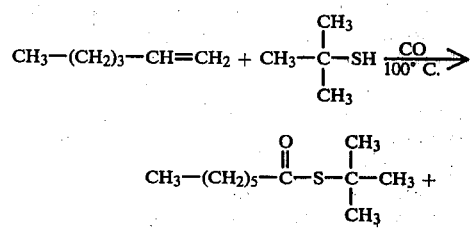

The following example is further illustrative of the present invention. The reactants and other specific ingredients are presented as being typical, and various modifications can be devised in view of the foregoing disclosure within the scope of the invention.

All catalyst solutions were prepared under prepurified nitrogen employing standard anaerobic techniques. A standard 300 cc magnedrive 316 SS autoclave from Autoclave Engineers was used for pressure reactions. Gas was fed into the autoclave from a one liter storage vessel through a pressure regulator to maintain constant autoclave pressure.

The autoclave was also equipped with two 150 ml cylinders to allow addition of liquids into the autoclave while under pressure. The autoclave was evacuated to <2 mm Hg before each experiment to collect foreign condensable materials into a −196° C. trap. The reactor and tubing were flushed with carbon monoxide before each run.

EXAMPLE

This Example illustrates a typical procedure in accordance with the present invention with respect to the production of t-butyl thioloheptanoate.

Into a nitrogen flushed flask was sequentially placed palladium(II) acetate (0.9 g, 4.0 mmole), 20 ml of dry deoxygenated tetrahydrofuran and triisopropylphosphine (0.8 ml, 0.7 g, 4.5×10$^{-3}$ mole) and 0.1 ml acetic acid. Upon stirring this mixture at room temperature for 15 minutes, a deep red-brown solution resulted which constituted the catalyst solution.

The reactants 1-hexene (37.4 ml, 25.2 g) and t-butylthiol (25.0 ml, 20.0 g) were added, and tetradecane (12.5 ml, 4.8×10$^{-3}$ mole) was included as a g.c. internal standard.

A 300 ml 316 SS magnedrive autoclave was flushed with CO and charged at room temperature with the reaction solution. The CO pressure in the reactor was maintained at 750 psi fed from a one liter storage vessel. The reactor temperature was brought to 100° C. as quickly as possible (about 0.5 hour) and stabilized at this temperature.

The reaction was followed as a function of time by observing both the change in pressure in the one liter storage vessel and the appearance of products by g.c. A 1 ml sample was taken from a bottom liquid sampling tap on the autoclave at a given time. This sampling line was washed with pentane and flushed with nitrogen after each sample was taken.

Reaction products were separated and isolated by prep g.c. on a 10-foot, ⅜ inch, aluminum column packed with 8% Dexil 300 on Anakrom Q 60/80 mesh(Supelco Inc.).

A typical plot for the appearance of t-butyl thioloheptanoate and t-butyl 2-methylthiolohexanoate is shown in the FIGURE. The ratio of t-butyl thioloheptanoate to t-butyl 2-methylthiolohexanoate was about 11/1 throughout the run. Data corresponding to the FIGURE are summarized in the Table.

The initial charge consisted of 0.30 mole of 1-hexene, 4 mmole of Pd(OAc)$_2$/(isopropyl)$_3$P and 750 psia carbon monoxide, and the reaction temperature was 100° C.

Other experimental efforts demonstrated that the rate of hydroesterification of 1-alkene with carbon monoxide and hindered thiol compound was not inhibited by an excess of thiol reactant, but the rate was reduced when the thiol reactant was kept at a minimum in the reaction medium.

The results indicated that the reaction order in thiol reactant was positive, and that the selectivity to linear thiolester product was not thiol concentration dependent.

It was also observed that at a higher reaction rate (conducted over a period of 21 hours) the Linear/Branched ratio of thiolester products was about 10–12 while at a lower reaction rate (conducted over a period of 44 hours) the said L/B ratio was in the range of about 20–24.

TABLE

| Time (hour) | t-Butyl 2-methylthiolohexanoate (moles) | % (a) | t-Butyl thioloheptanoate (moles) | % (a) | Linear/Branched |
|---|---|---|---|---|---|
| 0.00 | 0 | 0 | 0 | 0 | — |
| 0.08 | 0 | 0 | 0 | 0 | — |
| 1.08 | 0 | 0 | 0.007 | 3.3 | — |
| 2.08 | 0.002 | 0.9 | 0.025 | 11.3 | 12.5 |
| 3.08 | 0.004 | 1.7 | 0.041 | 18.7 | 10.2 |
| 4.08 | 0.005 | 2.2 | 0.057 | 26.1 | 11.4 |
| 5.08 | 0.006 | 2.8 | 0.071 | 32.2 | 11.8 |
| 6.33 | 0.008 | 3.5 | 0.087 | 39.4 | 10.9 |
| 8.83 | 0.010 | 4.5 | 0.113 | 51.3 | 11.3 |
| 21.33 | 0.015 | 7.1 | 0.173 | 78.8 | 11.5 |

(a) Based on t-butylthiol initial (0.22 mole).

What is claimed is:

1. A process for hydroesterification of 1-alkene which consisting essentially of (1) reacting 1-alkene with carbon monoxide and hindered thiol compound in a liquid medium containing a halide-free catalyst complex of palladium and tertiary hydrocarbylphosphine ligand; and (2) recovering alkyl thioloalkanoate product.

2. A process in accordance with claim 1 wherein the 1-alkene reactant in step (1) is a normal 1-alkene containing between about 2–12 carbon atoms.

3. A process in accordance with claim 1 wherein the thiol reactant in step (1) is a secondary or tertiary thiol compound containing between about 3–30 carbon atoms and 1–2 thiolo groups.

4. A process in accordance with claim 1 wherein the carbon monoxide reactant in step (1) is provided at a partial pressure between about 300–2000 psi.

5. A process in accordance with claim 1 wherein the liquid medium in step (1) comprises an organic solvent solution of reactants and catalyst complex.

6. A process in accordance with claim 1 wherein the catalyst complex in step (1) is provided in at least a catalytic quantity, and the mole ratio of 1-alkene to catalyst complex is at least 1:1 or higher.

7. A process in accordance with claim 1 wherein the palladium and tertiary phosphine ligand in the step (1) liquid medium are in a ratio between about 1–20 moles of tertiary phosphine ligand per gram atom of palladium metal.

8. A process in accordance with claim 1 wherein the step (1) reaction is conducted at a temperature between about 50°–180° C. for a reaction period between about 0.5–50 hours.

9. A process in accordance with claim 1 wherein the step (1) reaction is conducted at a pressure between about 300–3000 psi.

10. A process in accordance with claim 1 wherein the 1-alkene reactant in step (1) is 1-butene and the recovered product in step (2) is alkyl thiolopentanoate.

11. A process in accordance with claim 1 wherein the 1-alkene reactant in step (1) is 1-hexane and the product recovered in step (2) is alkyl thioloheptanoate.

12. A process in accordance with claim 1 wherein the 1-alkene reactant in step (1) is 1,4-hexadiene and the product recovered in step (2) is alkyl thiolohept-5-enoate.

13. A process in accordance with claim 1 wherein the thiol reactant in step (1) is 1,1-dimethylethanethiol.

14. A process in accordance with claim 1 wherein the thiol reactant in step (1) is 2-butanethiol.

15. A process in accordance with claim 1 wherein the thiol reactant in step (1) is 2-tridecanethiol.

16. A process in accordance with claim 1 wherein the thiol reactant in step (1) is cyclohexanethiol.

17. A process in accordance with claim 1 wherein the thiol reactant in step (1) is 1,1,1-triphenylmethanethiol.

18. A process in accordance with claim 1 wherein the palladium component in the step (1) catalyst complex is palladium diacetate.

19. A process in accordance with claim 1 wherein the palladium component in the step (1) catalyst complex is bis-(1,5-diphenyl-3-pentadienone)palladium(o).

20. A process in accordance with claim 1 wherein the tertiary phosphine ligand in the step (1) catalyst complex is trialkylphosphine.

21. A process in accordance with claim 1 wherein the tertiary phosphine ligand in the step (1) catalyst complex is triisopropylphosphine.

22. A process in accordance with claim 1 wherein the tertiary phosphine ligand in the step (1) catalyst complex is tri-n-butylphosphine.

23. A process in accordance with claim 1 wherein the tertiary phosphine ligand in the step (1) catalyst complex is tri-secondary-butylphosphine.

24. A process in accordance with claim 1 wherein the tertiary phosphine ligand in the step (1) catalyst complex is tricyclohexylphosphine.

25. A process in accordance with claim 1 wherein the tertiary phosphine ligand in the step (1) catalyst complex is a mixture of tertiary phosphines.

26. A process in accordance with claim 1 wherein the pH of the liquid medium in step (1) is maintained in a range between about 1–6 during the hydroesterification reaction.

27. A process in accordance with claim 1 wherein an acidic pH is provided in the step (1) liquid medium by the inclusion of a soluble carboxylic acid.

28. A process in accordance with claim 1 wherein a polymerization inhibitor is present in the step (1) liquid medium.

29. A process in accordance with claim 1 wherein a liquid fraction containing catalyst complex is recovered in step (2) and recycled to step (1).

* * * * *